(12) United States Patent
Lenneman

(10) Patent No.: US 12,426,829 B2
(45) Date of Patent: Sep. 30, 2025

(54) LONGITUDINAL DRIVER MONITORING FOR MEDICAL CONDITIONS: COGNITIVE IMPAIRMENTS

(71) Applicant: Toyota Motor Engineering & Manufacturing North America, Inc., Plano, TX (US)

(72) Inventor: John K. Lenneman, Okemos, MI (US)

(73) Assignees: TOYOTA MOTOR ENGINEERING & MANUFACTURING NORTH AMERICA, INC., Plano, TX (US); TOYOTA JIDOSHA KABUSHIKI KAISHA (JP)

( * ) Notice: Subject to any disclaimer, the term of this patent is extended or adjusted under 35 U.S.C. 154(b) by 393 days.

(21) Appl. No.: 17/891,059

(22) Filed: Aug. 18, 2022

(65) Prior Publication Data

US 2024/0057931 A1 Feb. 22, 2024

(51) Int. Cl.
| | | |
|---|---|---|
| A61B 5/00 | (2006.01) | |
| A61B 5/11 | (2006.01) | |
| A61B 5/16 | (2006.01) | |
| A61B 5/18 | (2006.01) | |

(52) U.S. Cl.
CPC .......... *A61B 5/4088* (2013.01); *A61B 5/0022* (2013.01); *A61B 5/1114* (2013.01); *A61B 5/163* (2017.08); *A61B 5/18* (2013.01); *A61B 5/4803* (2013.01); *A61B 5/6893* (2013.01); *A61B 5/7246* (2013.01); *A61B 2503/22* (2013.01); *A61B 2560/0242* (2013.01)

(58) Field of Classification Search
CPC ..... A61B 5/4088; A61B 5/163; A61B 5/0022; A61B 5/1114; A61B 5/18; A61B 5/4803; A61B 5/6893; A61B 5/7246; A61B 2503/22; A61B 2560/0242
USPC ........................................................ 340/576
See application file for complete search history.

(56) References Cited

U.S. PATENT DOCUMENTS

| | | | |
|---|---|---|---|
| 7,394,393 B2 | 7/2008 | Zhang et al. | |
| 7,515,054 B2 | 4/2009 | Torch | |
| 7,805,224 B2 | 9/2010 | Basson et al. | |
| 8,016,416 B1 | 9/2011 | Straus | |
| 8,384,534 B2 * | 2/2013 | James ................... | B60W 50/14 |
| | | | 342/107 |
| 9,122,775 B2 * | 9/2015 | Schunder ............... | G16H 40/67 |
| 9,223,837 B2 | 12/2015 | Djugash | |
| 10,426,393 B2 | 10/2019 | Bosworth et al. | |
| 10,449,968 B2 | 10/2019 | Shaikh et al. | |

(Continued)

OTHER PUBLICATIONS

Carr et al., *The Role of Eye Tracking Technology in Assessing Older Driver Safety*, Jun. 7, 2020, Geriatrics 2020, 14 pages.

(Continued)

*Primary Examiner* — Naomi J Small
(74) *Attorney, Agent, or Firm* — Snell & Wilmer LLP

(57) ABSTRACT

A system for detecting a cognitive status of a driver of a vehicle includes a first sensor configured to detect vehicle performance data, a second sensor configured to detect driver condition data, and an electrical control unit (ECU) coupled to the first sensor and the second sensor. The ECU is configured to receive the vehicle performance data corresponding to the cognitive status of the driver, receive the driver condition data corresponding to the cognitive status of the driver, and transmit the vehicle performance data and the driver condition data to a remote device.

20 Claims, 3 Drawing Sheets

(56) References Cited

U.S. PATENT DOCUMENTS

| | | | |
|---|---|---|---|
| 10,540,557 B2 | 1/2020 | Cordell et al. | |
| 10,956,721 B2 | 3/2021 | Tusch | |
| 11,787,417 B2 * | 10/2023 | Fields | B60W 60/005 |
| | | | 340/576 |
| 2012/0256749 A1 * | 10/2012 | Rao | A61B 5/0022 |
| | | | 701/1 |
| 2017/0236120 A1 * | 8/2017 | Herlihy | G06Q 20/065 |
| | | | 705/67 |
| 2017/0263120 A1 * | 9/2017 | Durie, Jr. | G08G 1/205 |
| 2018/0178766 A1 * | 6/2018 | Oba | B60T 7/22 |
| 2019/0038204 A1 * | 2/2019 | Beck | A61B 5/024 |
| 2019/0061772 A1 * | 2/2019 | Prinz | B60K 28/06 |
| 2021/0291650 A1 * | 9/2021 | Minjeur | A61B 5/0002 |
| 2023/0036776 A1 * | 2/2023 | Mussa | B60W 60/0016 |

OTHER PUBLICATIONS

Nilsson et al., *Vehicle Driver Monitoring—Sleepiness and Cognitive Load,* 2017, VTI rapport937A, 69 pages.

Schall Jr.et al., *Augmented Reality Cues and Elderly Driver Hazard Perception,* Human Factors, vol. 55, No. 3, Jun. 2013, pp. 643-658.

Ball et al., *Visual Attention Problems as a Predictor of Vehicle Crashes in Older Drivers,* Investigative Ophthalmology & Visual Science, Oct. 1993, vol. 34, No. 11, pp. 3110-3123.

* cited by examiner

LONGITUDINAL DRIVER MONITORING FOR MEDICAL CONDITIONS: COGNITIVE IMPAIRMENTS

BACKGROUND

Field

The present disclosure relates to systems and methods for providing detection and monitoring of disease progression and, more particularly, for collecting data regarding the cognitive functions of a driver.

Description of the Related Art

Cognitive impairments that result from disease (e.g., Alzheimer's, dementia, etc.) are difficult to detect in early stages. Further, late detection allows the disease to manifest and become difficult to mitigate. As a result, individuals with such disease experience negative effects on mobility and quality of life, occasionally leading to death at an earlier age. Early detection could lead to increases in quality of life for a longer period of time. Additionally, early detection could lead to a reduction in healthcare costs.

Currently, diagnoses and tracking of cognitive impairments are conducted through clinical assessments (e.g., MMSE and mini-cog test), neuroimaging (e.g., MM or CT), and/or self-reporting (e.g., reporting personal experiences or family history). Unfortunately, by the time clinical assessments can detect cognitive impairment, the dementia, for instance, is close to setting in or already has. Further, neuroimaging tests can be expensive and conducted infrequently, and self-reporting may be unreliable.

However, research has shown that driver's show measurable changes in behavior that reliably index disease progression. Thus, there is a need for systems and methods for detecting whether a driver is demonstrating those changes in order to enable earlier detection and monitoring of disease progression.

SUMMARY

Described herein is a system for detecting a cognitive status of a driver of a vehicle. The system includes a first sensor configured to detect vehicle performance data, a second sensor configured to detect driver condition data, and an electrical control unit (ECU) coupled to the first sensor and the second sensor. The ECU is configured to receive the vehicle performance data corresponding to the cognitive status of the driver, receive the driver condition data corresponding to the cognitive status of the driver, and transmit the vehicle performance data and the driver condition data to a remote device.

Also described is a method for detecting a cognitive status of a driver of vehicle. The method includes detecting vehicle performance data corresponding to the cognitive status of the driver, detecting driver condition data corresponding to the cognitive status of the driver, and transmitting the vehicle performance data and the driver condition data to a remote device.

BRIEF DESCRIPTION OF THE DRAWINGS

The features, obstacles, and advantages of the present invention will become more apparent from the detailed description set forth below when taken in conjunction with the drawings, wherein.

DETAILED DESCRIPTION

Described herein are systems and methods for collecting driver data to provide insights into onset of cognitive impairment, progression of disease, and effectiveness of medication/treatment. For instance, driver data can include driving performance, such as a decrease in driving at night, decrease in driving overall, avoiding highway, etc., and behavior data, such as glances/fixation, head movements, etc. The systems and methods provide several benefits and advantages such as providing quantitative data to healthcare providers for monitoring and early detection of diseases that cause cognitive impairment.

An exemplary system includes at least one sensor (e.g., face cameras) to capture sensory data such as monitoring daily and longitudinal changes in visual scanning data (e.g., fixations) and compares the sensory data to individual baselines. The system further includes sensors to capture behavioral data such as driving behavior (e.g., daily and longitudinal changes in gross and fine motor movements (e.g., head movements)) and driving performance (e.g., hard braking events) and compares the driving behavior and the driving performance to individual baselines. In other words, the system is a driver monitoring system that tracks daily or longitudinal driving patterns or behaviors, monitors eye gaze, uses longitudinal data related to the driver's eye fixation, etc. The exemplary system combines the visual scanning data with data collected about driving behavior (time of driving, amount of driving, location of driving, etc.) and driving performance (e.g., changes in hard braking event frequency, abrupt lane changes, violating driving laws, etc.) to create an integrated report for healthcare stakeholders.

Figure 1:
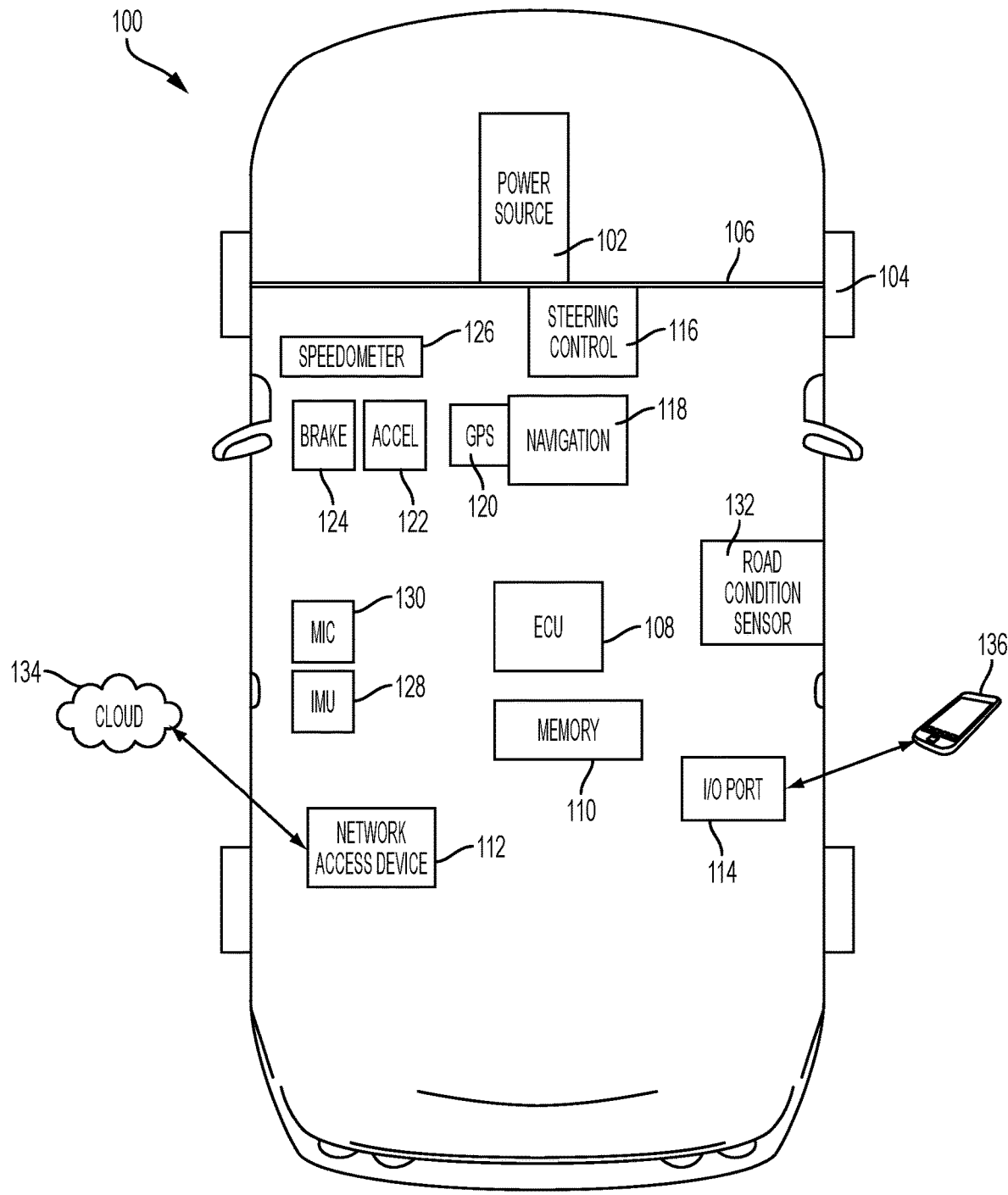
FIG. 1 is a block diagram of a vehicle having sensors for detecting vehicle performance data, driver condition data and road condition data and having an electronic control unit (ECU) for collecting the detected data according to an embodiment of the present invention.

Turning to FIG. 1, a vehicle 100 is illustrated, according to an exemplary embodiment. The vehicle 100 includes a power source 102, wheels 104, an axle 106, an ECU 108 and a memory 110. The vehicle 100 also includes a network access device 112, an input/output port (I/O port) 114, a steering control unit 116, a navigation unit 118 and a GPS unit 120. The vehicle 100 also includes an acceleration pedal 122 and a brake pedal 124, a speed sensor 126, an inertial measurement unit (IMU) 128, a microphone 130 and a road condition sensor 132.

The power source 102 may be any power source capable of providing torque to the wheels 104 via the axle 106. For example, the power source 102 may include one or more of an engine, a motor/generator, batteries, a fuel cell or the like.

The ECU 108 can include one or more processors or controllers which may be specifically designed for automotive systems. The functions of the ECU 108 can be implemented in a single ECU or in multiple ECUs. For example, the vehicle 100 may include a first ECU that performs functions related to autonomous driving and a second ECU that performs functions corresponding to the monitoring of a driver. The ECU 108 may receive data from components of the vehicle 100, may make determinations based on the received data and may control the operation of components based on certain determinations.

The memory 110 may include any non-transitory memory known in the art. In that regard, the memory 110 may store machine-readable instructions usable by the ECU 108 and may store any other data as requested by the ECU 108.

The network access device 112 may include any device capable of communicating with an external device or network. For example, the network access device 112 may communicate with the cloud 134 via 3G protocols, 4G protocols, 802.11 (Wi-Fi) protocols, a Dedicated Short-Range Communications (DSRC, usable in vehicle-to-infrastructure or vehicle-to-vehicle communications) port or the like.

The I/O port 114 can include any I/O port capable of receiving data from and/or transferring data to another device. The I/O port 114 may connect to other devices via a wired or wireless interface. For example, the I/O port 114 may be a USB port, a Wi-Fi port, a Bluetooth port or the like. The I/O port 114 may transmit data to and receive data from an external device such as a mobile device 136 (i.e., a cell phone, a tablet or the like). In that regard, the ECU 108 can communicate with the mobile device 136 via the I/O port 114.

One or both of the network access device 112 or the I/O port 114 may communicate with other vehicles or infrastructure. In that regard, one or both of the network access device 112 or the I/O port 114 may be used in vehicle-to-other device communications such as via a DSRC port. For example, the vehicle 100 may communicate with another vehicle or a network using vehicle-to-vehicle communications or vehicle-to-infrastructure communications via the network access device 112 or the I/O port 114.

The steering control unit 116 may be coupled to the axle 106 and/or to individual wheels 104. The steering control unit 116 may include an actuator or actuators for changing the position of the axle 106 and/or wheels 104 to control steering of the vehicle 100. For example, the steering control unit 116 may be a power steering system.

The ECU 108 may be coupled to the steering control unit 116 and control the steering of the vehicle via the steering control unit 116. The ECU 108 may also be coupled to the power source 102 and control power output of the power source 102. In that regard, the vehicle 100 may be autonomous meaning that the ECU 108 controls driving operations.

The GPS unit 120 may include one or more GPS receivers capable of receiving location data corresponding to a current location of the vehicle 100. In that regard, the ECU 108 can determine a current location of the vehicle 100 based on data from the GPS unit 120.

The navigation unit 118 may be coupled to the GPS unit 120 and may include an interface such as a display, one or more speakers, buttons, dials, a touchscreen, a touchpad, a remote control interface device or the like. The navigation unit 118 may receive a desired location or address via the interface and may provide navigation instructions from the current location of the vehicle to the desired location or address. In some embodiments, the functions of the navigation unit 118 may be performed by other components of the vehicle 100 such as a separate input/output device (not shown) and the ECU 108.

The acceleration pedal 122 is used by a driver to control acceleration of the vehicle 100. The acceleration pedal 122 may include or be coupled to a sensor (not shown) that detects movement of the acceleration pedal 122 corresponding to a requested amount of acceleration. The ECU 108 may be coupled to the sensor and control torque output of the power source 102 based on the movement of the acceleration pedal 122.

The brake pedal 124 is used by the driver to control braking of the vehicle 100. The brake pedal 124 may include or be coupled to a sensor (not shown) that detects movement of the brake pedal 124 corresponding to a requested braking operation. The ECU 108 may be coupled to the sensor and control braking of the vehicle based on the relative position of the brake pedal 124.

The speed sensor 126 may include a sensor and/or logic for detecting or determining the speed of the vehicle 100. For example, the speedometer may include a ground speed sensor, an accelerometer, an angular velocity sensor or the like.

The IMU 128 may include any sensor or sensors capable of detecting inertial movement of the vehicle 100. For example, the IMU 128 may include a gyroscope, an accelerometer, a magnetometer or the like. The IMU 128 may detect data corresponding to an acceleration of the vehicle 100 in one or more directions.

The microphone 130 may include any microphone or other audio sensor capable of detecting audio data. The microphone 130 may be positioned within the vehicle 100 so as to detect audio data corresponding to speech of a driver. In some embodiments, the microphone 130 may be included with the navigation unit 118 and used as an input device for the navigation unit 118 and/or the ECU 108.

The road condition sensor 132 may include any sensor capable of detecting data corresponding to a road condition. The data may include, for example, weather information such as temperatures, moisture or ambient light; qualities of the road such as whether the road is paved, dirt or gravel; traffic data corresponding to an amount of traffic on the road; speed limit data corresponding to a speed limit; or the like. In some embodiments, road condition data may be received from the cloud 134 or a mobile device 136 instead of, or in addition to, the road condition sensor 132.

Figure 2:
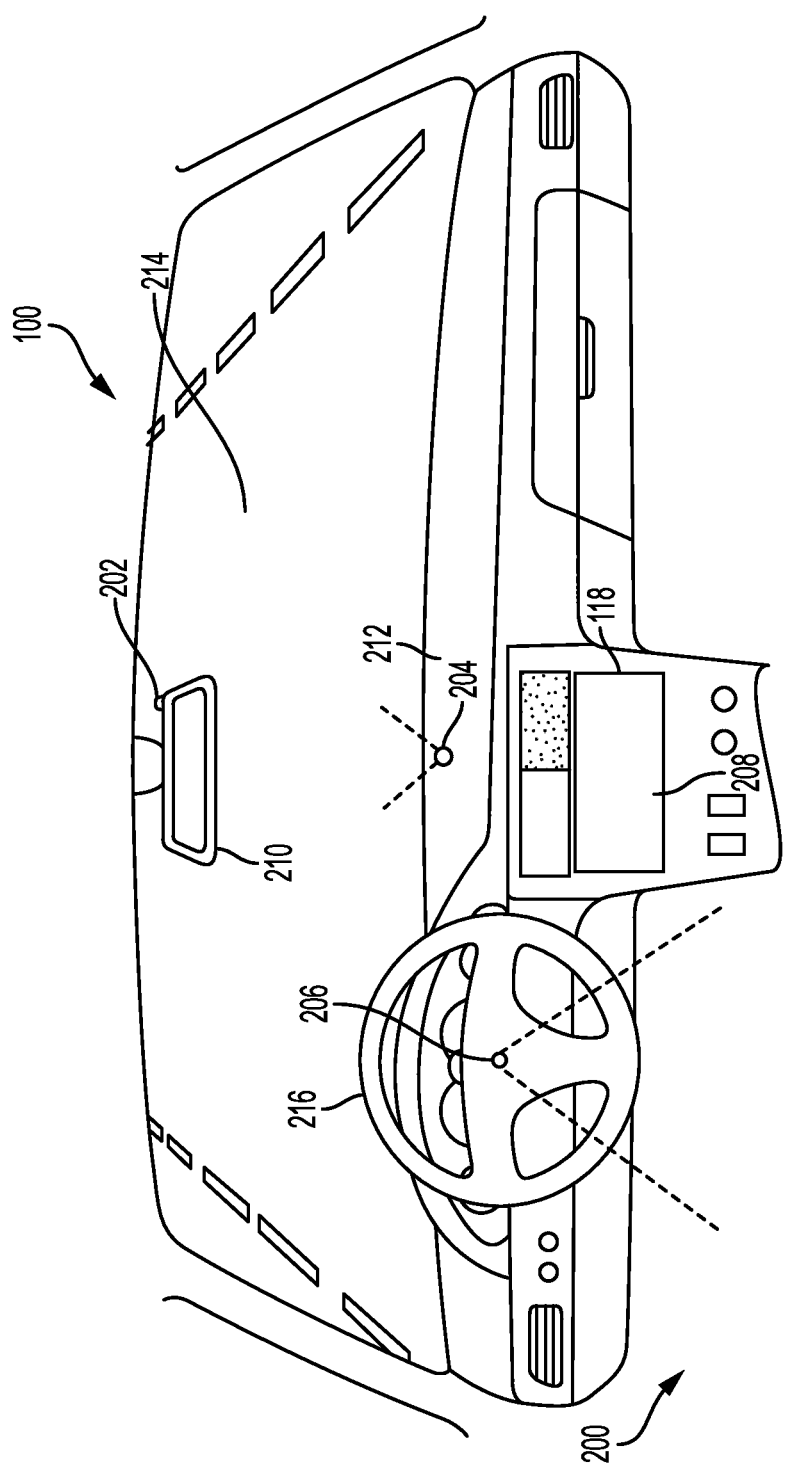
FIG. 2 is a drawing of an interior cabin of the vehicle of FIG. 1 including a driver-facing camera and a forward-facing camera according to an embodiment of the present invention.

Referring to FIGS. 1 and 2, a view of an interior 200 of the vehicle 100 shows additional components of the vehicle 100. As shown, the vehicle 100 also includes an ambient light sensor 202, a forward-facing camera 204 and a driver-facing camera 206. Furthermore, the navigation unit 118 is shown as having a touchscreen interface 208.

The ambient light sensor 202 is designed to detect ambient light of the environment of the vehicle 100. The ambient light sensor 202 may detect whether the sun is shining brightly, whether it is currently cloudy, whether it is nighttime or the like. The ambient light sensor 202 may be positioned within the interior 200 at a location that is exposed to ambient light, such as on a rear-view mirror 210 or a dashboard 212 of the vehicle 100.

The forward-facing camera 204 may include one or more cameras and is designed to detect or capture image data corresponding to an environment of the vehicle 100. The forward-facing camera 204 may face forward of the vehicle and detect data corresponding to a road 214. The forward-facing camera 204 may detect data such as whether the road 214 is paved, whether there is traffic on the road 214, whether the vehicle 100 is approaching a lane marker or the like. In that regard, the forward-facing camera 204 and the ambient light sensor 202 may each be road condition sensors.

The forward-facing camera 204 may be positioned at a location in which it can detect data corresponding to the road in front of the vehicle 100. For example, the forward-facing camera 204 may be positioned on the dashboard 212 or the rear-view mirror 210 of the vehicle 100.

The driver-facing camera 206 may include one or more cameras and is designed to detect or capture image data corresponding to the driver. In some embodiments, the driver-facing camera 206 may include infrared sensors or other sensors capable of detecting image data in various levels of light such that image data may be detected regardless of current levels of light in the interior 200.

The driver-facing camera 206 is directed towards the driver's seat and positioned such that it can detect image data corresponding to at least a portion of the driver. For example, the driver-facing camera 206 may be positioned so as to detect image data corresponding to the driver's head and face. In that regard, the driver-facing camera 206 can detect facial expressions of the driver, a direction of the driver's gaze, whether the driver is staring at a particular point, whether the driver's eyes are droopy or the like.

The driver-facing camera 206 may also or instead be positioned to detect image data corresponding to the driver's body. In that regard, the driver-facing camera 206 can detect a body position of the driver, whether the driver is leaning or slumping or the like. In some embodiments, two or more driver-facing cameras may be included to detect data corresponding to different body parts of the driver.

The driver-facing camera 206 may be positioned in such a location as to be able to detect at least a portion of the driver. For example, the driver-facing camera 206 may be positioned on a steering wheel 216, the dashboard 212, the rear-view mirror 210 or the like.

The steering wheel 216 may be coupled to a sensor (not shown) for detecting a current steering position of the steering wheel 216. In that regard, the ECU 108 may receive requested steering operations from the sensor. The ECU 108 may control operation of the steering control unit 116 based on the requested steering operations.

The ECU 108 may be coupled to the components of the vehicle 100 and receive vehicle performance data, driver condition data and road condition data. The vehicle performance data includes data corresponding to the driving and handling of the vehicle 100. For example, the vehicle performance data may include speed data from the speed sensor 126, acceleration data from the IMU 128, braking data from the brake pedal 124, steering data from the steering wheel 216, lane departure data from the forward-facing camera 204 or the like.

Each of the vehicle performance data may be used as factors to detect a cognitive status of the driver of the vehicle 100. "Cognitive status" as used herein is an accumulation of data that is collected over time indicating changes (i.e., degradations) in driving performance, visual scanning, etc., that are associated with changes in cognition. For example, a constant speed of the vehicle 100 may indicate that the driver is functioning well as opposed to a reading indicating a variable speed. Likewise, smooth accelerations may indicate that the driver is functioning well as opposed to a reading indicating hard or reactionary accelerations; smooth and early braking may indicate that the driver is functioning well as opposed to a reading indicating hard and reactionary braking; smooth steering may indicate that the driver is functioning well as opposed to a reading indicating reactionary steering; and a lack of unwarranted lane departures may indicate that the driver is functioning well as opposed to a reading indicating multiple unwarranted lane departures.

The driver condition data includes data corresponding to the driver's condition or state within the vehicle. For example, the driver condition data may include facial expressions of the driver detected by the driver-facing camera 206, body positions of the driver detected by the driver-facing camera 206, eye movement of the driver detected by the driver-facing camera 206, speech patterns of the driver detected by the microphone 130, or the like. In some embodiments, the driver condition data may be detected by sensors that are not included with the vehicle 100. For example, the driver condition data may include biometric data from wearable devices, data detected by sensors embedded within clothing or any other data detected by a device that is part of the internet of things (IoT).

Each of the driver condition data may also or instead be used as a detection of the cognitive status of the driver of the vehicle 100. For example, an alert expression on the driver's face may indicate that the driver is functioning well as opposed to a reading indicating a drowsy expression. Likewise, an upright body position of the driver may indicate that the driver is functioning well as opposed to a reading indicating a slouched body position; occasional side-to-side eye movement of the driver's eyes may indicate that the driver is functioning well as opposed to a reading indicating a continuous stare in one direction; and clear and intelligible speech may indicate that the driver is functioning well as opposed to a reading indicating slurred speech.

The road condition data includes data corresponding to an environment of the vehicle 100 and/or a road on which the vehicle 100 is traveling. For example, the road condition data may include weather data from the road condition sensor 132, the forward-facing camera 204, the ambient light sensor 202, or the like. In some embodiments, the weather data may also or instead be received from the cloud 134, via the user's mobile device 136 or from a vehicle-to-other device system (such as vehicle-to-vehicle or vehicle-to-infrastructure). The road condition data may also include current traffic along the driver's route detected by the forward-facing camera 204. In some embodiments, the current traffic data may also or instead be received from the cloud 134, the user's mobile device 136 and/or from the vehicle-to-other device system. The road condition data may also include a speed limit of a road of the vehicle detected by the forward-facing camera 204, received from the cloud 134, the user's mobile device 136 and/or the vehicle-to-other device system. The road condition data may also include data indicating a road surface of a current road received from the forward-facing camera 204, received from the cloud 134, the user's mobile device 136 and/or the vehicle-to-other device system.

Each of the road condition data may be used as a factor in detecting the cognitive status of the driver of the vehicle 100. For example, if the driver only drives when the weather is sunny, such data may be indicative of the driver feeling uncomfortable driving in the dark to a cognitive impairment. Similarly, if the driver only drives at a particular time of day, such data may be indicative of the driver feeling uncomfortable driving during high traffic times due to a cognitive impairment. Further, if the driver avoids highways, such data may be indicative of the driver feeling uncomfortable driving at high speeds due to a cognitive impairment.

The ECU 108 may also store previous vehicle performance data, driver condition data and road condition data. The ECU 108 may determine a baseline value of the driver that corresponds to the initial behavior and patterns of the driver based on the vehicle performance data and the driver condition data. As such, a change in any of the vehicle performance data and the driver condition data may indicate an onset of the cognitive impairment and/or a progression rate of the cognitive impairment. The ECU 108 may continuously learn and improve the accuracy of the rate of increase as more and more data is collected and analyzed by a healthcare provider. For instance, the healthcare provider may be recommended that the driver not drive when a frequency or amount of changes is greater than a predetermined threshold.

The ECU 108 may send the performance data and the driver condition data to a healthcare provider (e.g., a doctor, a neurologist, an Alzheimer's specialist, etc.) via the network access device 112. For instance, the network access device 112 may communicate the performance data and the driver condition data to the cloud 134 wherein the healthcare provider may access the data. In various embodiments, the cloud 134 may conduct cloud-based data reduction/synthesis of the performance data and the driver condition data, resulting in a cloud-based report generation. The data reduction/synthesis may provide insights into the visual scanning behavior and/or driving behavior, decisions, etc. In various embodiments, the ECU 108 may send the results to the healthcare provider when the frequency or amount of changes is greater than the predetermined threshold. As such, the ECU 108 may raise an alarm to healthcare provider. In various embodiments, the ECU 108 may receive a request from the healthcare provider to collect the performance data and the driver condition data and send the results to the healthcare provider. The healthcare provider may then compare to previous data received from the vehicle 100 and determine the cognitive status of the driver (e.g., possible progression or successful mitigation through effective treatment).

Figure 3:
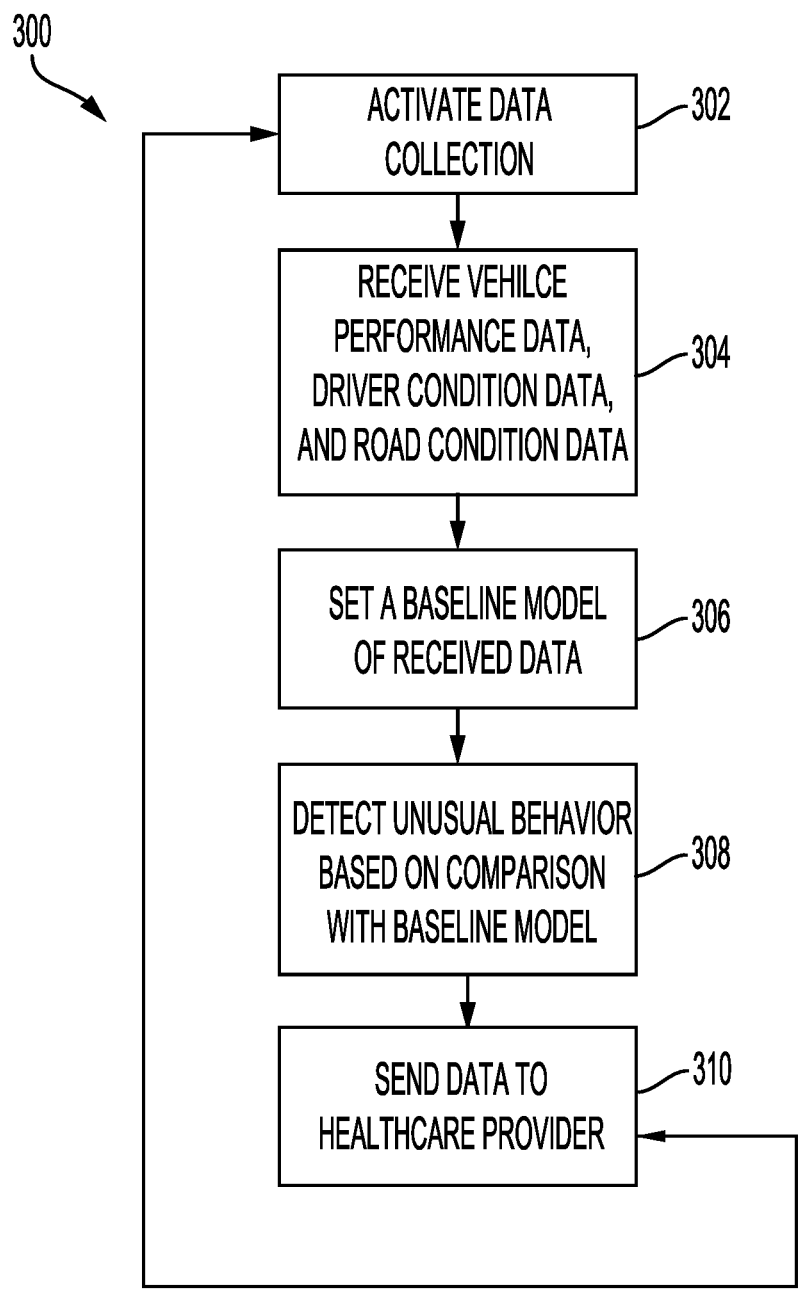
FIG. 3 is a flowchart illustrating a method for collecting cognitive status of a driver of a vehicle according to an embodiment of the present invention.

Turning now to FIG. 3, a method 300 for detecting a cognitive status of a driver of a vehicle is shown. The method 300 may be performed by a vehicle similar to the vehicle 100 of FIG. 1 and utilizing similar components. At 302, data collection is activated. For instance, the data collection may be activated by an alarm raised via self-awareness, family history, a recent diagnosis, etc. The data collection may be requested by the driver or a healthcare provider of the driver. For instance, the vehicle may receive data from an external device such as a mobile device/mobile application.

At 304, an ECU of the vehicle detects and/or receives vehicle performance data, driver condition data and road condition data. The vehicle performance data, driver condition data and road condition data are detected and/or received as discussed above with reference to FIGS. 1 and 2. For instance, sensors may be configured to monitor daily and longitudinal changes in visual scanning data (e.g., fixations). For instance, when the driver is stopping at a stop sign, the sensor detects if the driver is appropriately looking at them, and properly responding (e.g., the driver appeared to have looked at the stop sign but then continued to driver through the intersection). Additionally, sensors may be configured to monitor daily and longitudinal changes in gross and fine motor movements (e.g., head movements). For instance, as described herein, an image sensor may detect the driver is not looking at the road. Further, for instance, as described herein, the steering control unit may sense erratic hand movements on the steering wheel. Inefficient fixations (e.g., too many and too long) and/or constant head movements are associated with cognitive impairment. As such, degradation in visual scanning and motor movements due to concentration issues occurs as cognitive impairment increases. Early reporting of these behaviors may result in early detection of a corresponding disease.

Moreover, sensors may be configured to monitor daily and longitudinal changes in driving behavior and driving performance (e.g., hard braking events). A navigation unit may be used to obtain navigational map information including a current location of the vehicle, a current time of day, driving routes, etc. The navigational map information may include other information, such as the current speed and direction of travel of the vehicle. The detection system 100 may use the navigational map information to assist in detect whether an activity is unusual, not normal or otherwise unordinary. For example, as described herein, the sensors may detect the driver is driving significantly above or below, or inconsistently, according to the posted speed limits. Further, for example, the sensors may detect the driver is depressing the brake pedal rapidly for no detectable reason (e.g., reported traffic). Significant changes in driving behavior and performance are seen as cognitive impairment progresses. Early reporting of these behaviors may result in early detection of a corresponding disease.

At 306, the ECU may collect vehicle performance data, driver condition data and road condition data over a period of time. Accordingly, a baseline or a baseline model of the driver and their corresponding behaviors is set. The baseline or the baseline model is used to predict, determine or otherwise detect unusual activities. The baseline or the baseline model may be based on the current location of the vehicle, the time of day, the weather, the navigational map information and/or one or more situational factors. The detection system may determine that the vehicle is traveling on a residential roadway based on the current location of the vehicle and the navigational map information, and in response, the detection system may select a baseline or baseline model that is specific to travel on roadways in residential areas, which may be different than travel on an interstate highway.

At 308, unusual activity based on a comparison between the driver's current activity and the baseline is detected. For example, if the speed of the vehicle is a continued acceleration into the intersection, whereas, the baseline motion of the vehicle is a deceleration to a full stop when the traffic signal indicates a stop or yield signal, the vehicle performance data and driver condition data is determined to be unusual. In another example, if an eye of the individual is moving side to side rapidly or unusually fixated on a point the vehicle performance data and driver condition data is determined to be unusual.

When detecting that the behavior is different than the baseline motion and/or unusual, an allowable tolerance may be considered. For example, on a bright clear sunny day and with few surrounding vehicles, a larger allowable tolerance in the speed of the vehicles in the cross-traffic may be allowed because the driver of the vehicle has a clear view of the cross-traffic. In another example, on the bright clear sunny day and with the few surrounding vehicles, the driver of the vehicle may be allowed to be more distracted than when the vehicle is surrounded by many vehicles and it is raining because the distraction presents less of a danger.

At 310, the ECU may send the acquired vehicle performance data and driver condition data to the healthcare provider. For instance, the data collected, as described herein, may be compiled, reduced and/or packaged for distribution to healthcare stakeholders. The healthcare provider may then analyze the data and determine next steps (e.g., diagnosis, treatment plan, continued monitoring, etc.). The data can also be distributed to or sent to family members. Prior to the data being sent to the healthcare provider or the family member, the vehicle performance data and the driver condition data may undergo a cloud-based synthesis. As such, a cloud-based report is sent to the healthcare provider or the family member. In various embodiments, the ECU may determine a rate of increase of the changed behavior and/or the changed behavior has reached a predetermined threshold. The ECU may determine the rate by analyzing previously-detected vehicle performance data, driver condition data and road condition data. In response, the ECU may send the acquired vehicle performance data and driver condition data to the healthcare provider or the family member. Depending on the next steps determined by the healthcare provider or the family member, monitoring vehicle performance data and driver condition data may continue. As such, method 300 continues back to 302.

Exemplary embodiments of the invention have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A system for detecting prolonged progression of a cognitive impairment due to a disease or syndrome of a driver of a vehicle, the system comprising:
   a first sensor configured to detect vehicle performance data;
   a second sensor configured to detect driver condition data; and
   an electrical control unit (ECU) coupled to the first sensor and the second sensor, and configured to:
      receive the vehicle performance data corresponding to a cognitive status of the driver, the vehicle performance data indicating when the driver is experiencing progression of the cognitive impairment, the cognitive impairment being due to the disease or syndrome;
      receive the driver condition data corresponding to the cognitive status of the driver, the driver condition data indicating when the driver is experiencing the progression of the cognitive impairment;
      calculate a baseline value corresponding to an initial behavior and pattern of the driver based on the vehicle performance data and the driver condition data;
      compare the vehicle performance data and the driver condition data to the baseline value to detect a change between (1) the vehicle performance data and the driver condition data and (2) the baseline value, the change indicating when the driver is experiencing a prolonged progression of the cognitive impairment; and
      based on the detected change, transmit a deviation signal to a remote device, the deviation signal indicating that a rate of increase of the detected change has reached or exceeded a predetermined threshold, the rate of increase indicating the driver is experiencing the prolonged progression of the cognitive impairment.

2. The system of claim 1, wherein the vehicle performance data includes at least one of vehicle speed data, acceleration data, braking data, steering data or lane departure data.

3. The system of claim 1, wherein the driver condition data corresponds to at least one of facial expressions of the driver, body positioning of the driver, eye movement of the driver or speech patterns of the driver.

4. The system of claim 1, further comprising a memory configured to store previously detected vehicle performance data and previously detected driver condition data.

5. The system of claim 4, wherein the ECU is configured to determine the baseline value based on the previously detected vehicle performance data and previously detected driver condition data stored in the memory.

6. The system of claim 1, further comprising a navigation unit configured to obtain navigational map information, the navigational map information including a current location of the vehicle, a current time of day, driving routes, a current speed of the vehicle, or a direction of travel of the vehicle.

7. The system of claim 6, wherein the ECU is further configured to identify unusual driver behavior based on the navigational map information.

8. The system of claim 1, further comprising a network access device configured to communicate with the remote device such that the ECU transmits the vehicle performance data and the driver condition data to the remote device via the network access device.

9. The system of claim 1, wherein the remote device is associated with a healthcare provider.

10. The system of claim 1, wherein the ECU is further configured to receive a request from the remote device to initiate the first sensor to detect the vehicle performance data and the second sensor to detect the driver condition data.

11. The system of claim 1, further comprising a third sensor configured to detect road condition data or an input/output port or a network access device configured to receive the road condition data, the road condition data corresponding to at least one of weather, traffic, a speed limit or a road surface and wherein the ECU is further configured to:
   receive the road condition data corresponding to the cognitive status of the driver; and
   transmit the road condition data to the remote device.

12. A method for detecting prolonged progression of a cognitive impairment due to a disease or syndrome of a driver of a vehicle, the method comprising:
   receiving a request from a remote device associated with a healthcare provider to initiate a first sensor to detect vehicle performance data and a second sensor to detect driver condition data;
   detecting the vehicle performance data corresponding to the cognitive impairment due to a disease or syndrome of the driver, the vehicle performance data indicating when the driver is experiencing progression of cognitive impairment, the cognitive impairment being due to the disease or syndrome;
   detecting the driver condition data corresponding to the cognitive impairment due to the disease or syndrome of the driver, the driver condition data indicating when the driver is experiencing the progression of the cognitive impairment;
   calculating a baseline value corresponding to an initial behavior and pattern of the driver based on the vehicle performance data and the driver condition data;
   comparing the vehicle performance data and the driver condition data to the baseline value to detect a change between (1) the vehicle performance data and the driver condition data and (2) the baseline value, the change indicating when the driver is experiencing a prolonged progression of the cognitive impairment; and based on the detected change, transmitting a deviation signal to the remote device, the deviation signal indicating that a rate of increase of the detected change has reached or exceeded a predetermined threshold, the rate of increase indicating the driver is experiencing the prolonged progression of the cognitive impairment.

13. The method of claim 12, wherein the vehicle performance data includes at least one of vehicle speed data, acceleration data, braking data, steering data or lane departure data.

14. The method of claim 12, wherein driver condition data corresponds to at least one of facial expressions of the driver, body positioning of the driver, eye movement of the driver or speech patterns of the driver.

15. The method of claim 12, further comprising storing previously detected vehicle performance data and previously detected driver condition data in a memory.

16. The method of claim 15, further comprising determining the baseline value based on the previously detected vehicle performance data and the previously detected driver condition data stored in the memory.

17. The method of claim 12, further comprising obtaining navigational map information from a navigation unit, the navigational map information including a current location of the vehicle, a current time of day, driving routes, a current speed of the vehicle, or a direction of travel of the vehicle.

18. The method of claim 17, further comprising identifying unusual driver behavior based on the navigational map information.

19. The method of claim 12, further comprising transmitting the vehicle performance data and the driver condition data to the remote device via a network access device.

20. The method of claim 12, further comprising:
detecting road condition data, the road condition data corresponding to at least one of weather, traffic, a speed limit or a road surface; and
transmitting the road condition data to the remote device.

* * * * *